United States Patent [19]

Nappholz et al.

[11] Patent Number: 5,766,227
[45] Date of Patent: Jun. 16, 1998

[54] EMI DETECTION IN AN IMPLANTABLE PACEMAKER AND THE LIKE

[76] Inventors: Tibor A. Nappholz, 8524 E. Jamison Ave., Englewood, Colo. 80112; Robert Whigham, 405 Pearl St., Boulder, Colo. 80302

[21] Appl. No.: 811,156

[22] Filed: Mar. 4, 1997

[51] Int. Cl.$^6$ ............................................. A61N 1/362
[52] U.S. Cl. ............................................................ 607/9
[58] Field of Search ............................ 607/9, 27; 128/901

[56] References Cited

U.S. PATENT DOCUMENTS

| | | | |
|---|---|---|---|
| 3,677,251 | 7/1972 | Bowers | 607/9 |
| 3,678,937 | 7/1972 | Cole et al. | 607/9 |
| 4,129,133 | 12/1978 | Imich et al. | 607/9 |
| 5,522,857 | 6/1996 | van Krieken | |

Primary Examiner—William E. Kamm
Assistant Examiner—George R. Evanisko
Attorney, Agent, or Firm—Gottlieb, Rackman & Reisman

[57] ABSTRACT

An implantable pacemaker receives electrical signals from a patient's heart through an electrode, the signals being either intrinsic cardiac signals or repetitive noise signals, due for instance to electromagnetic inference. The pacemaker includes circuitry for determining if the signals from the electrode are cardiac in origin or not by extracting certain signal characteristics from the signals. For example, the noise signals produced by EMI are repetitive, i.e., they have a fairly constant amplitude except for the initial peak. On the other hand cardiac signals have at most three peaks of decreasing amplitudes. These characteristics are used by the determined circuitry to differentiate between cardiac and noise signals. While this determination is taking place, the received signals are stored or delayed. Signals identified as cardiac signals are processed. The processed signals are compensated for the delay caused by the noise detection circuitry.

15 Claims, 5 Drawing Sheets

EMI DETECTION IN AN IMPLANTABLE PACEMAKER AND THE LIKE

BACKGROUND OF THE INVENTION

1. Field of Invention

This invention pertains to an implantable pacemaker and other implantable cardiac devices incorporating means for the detection and rejection of noise produced by electromagnetic interference (EMI).

2. Description of the Prior Art

Early pacemakers were somewhat susceptible to certain ambient electromagnetic radiation such as radiation produced by microwave devices. Improvements in modern day cardiac devices, including more effective filtering right at the input have successfully eliminated this susceptibility. However, the performance of pacemakers may still be affected by sudden onset of electromagnetic interference EMI induced, for example, by 50 or 60 Hz power sources and the like. This susceptibility is due to the fact that the intrinsic cardiac signals produced in a patient's heart have frequencies and amplitudes in the same range as the step induced EMI. Attempts at dealing with this interferences have not been very successful. See U.S. Pat. No. 5,522,857.

OBJECTIVES AND SUMMARY OF THE INVENTION

It is an objective of the present invention to provide an implantable cardiac device arranged and constructed to recognize repetitive extraneous signals such as, for example, EMI, even when sudden onset occurs.

A further objective is to provide a cardiac device constructed and arranged to ignore such extraneous signals in such a manner as not to interfere with the normal operation of the device.

A further objective is to ensure that the pacemaker passes the EMI test requirements set by CENELEC (a European regulatory organization) where sudden onset of EMI is used as test signals.

Yet a further objective is to provide an implantable device having the above-mentioned advantages but which can be constructed without requiring any additional components. Other objectives and advantages of the invention shall become apparent from the following description.

The present invention provides a sensor which detects noise by counting the number of signal peaks in a predetermined sensing window. If the number of peaks exceeds a preselected threshold, (such as three) the sensing is compromised. Therefore, sensing is terminated, and pacing is performed at a preselected rate. At the next checkup, the clinician detects this rate through an appropriate programmer and takes any necessary steps to eliminate the source of noise.

Briefly, a pacemaker made in accordance with this invention, includes means for sensing cardiac activity in a patient's heart, means for analyzing signals sensed in the cardiac chamber to differentiate between noise signals having certain predetermined, repetitive characteristics, and intrinsic cardiac signals and means for accepting the cardiac signals for further processing if they have not been identified as noise signals. Preferably the signals are analyzed by setting an inspection window after a first signal is sensed, and comparing the peak amplitudes of the signals sensed therein. If the number of these peaks are indicative of noise, then the received signals are ignored and a fallback pacing rate is provided, as discussed above.

DETAILED DESCRIPTION OF THE INVENTION

Figure 1A:
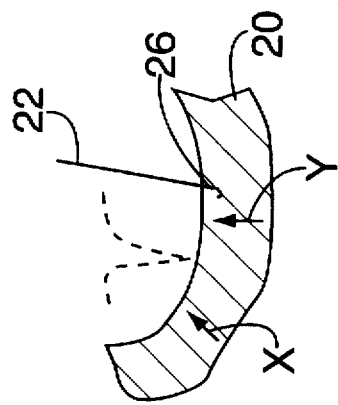
FIG. 1A shows one type of depolarization propagation through a cardiac tissue.

Typically, a depolarization waveform may propagate through a cardiac tissue either longitudinally or transversely. FIG. 1A shows a tissue 10 through which a longitudinal depolarization wave is traveling or propagating as indicated by arrow X. An electrode 10 is provided with a tip 14 imbedded in the tissue as shown for sensing cardiac activity. The distal end (not shown) an electrode 12 is coupled to a cardiac implant device (not shown). A typical electrical signal 16 detected by the cardiac implant through electrode 12 is shown (after filtering) in FIG. 1B. The signal 16 has a positive portion 16A, followed by a negative portion 16B, followed by a positive portion 16C.

Figure 1C:
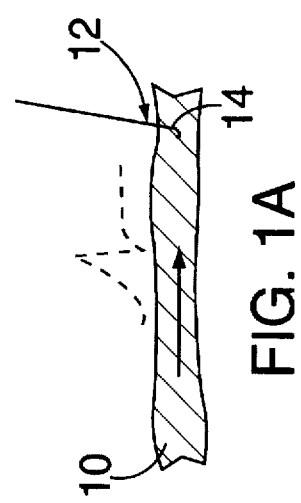
FIG. 1C shows another type of depolarization propagation through a cardiac tissue.

FIG. 1C shows a depolarization propagating transversely through tissue 20, as indicated by arrows X and Y. An electrode 22 with a tip 24 embedded in tissue 20 can be used a corresponding electrical signal 26 shown (after filtering) in FIG. 1D. This signal 26 has two negative portions 26A, 26C, separated by a positive section 26B.

Figure 1B:
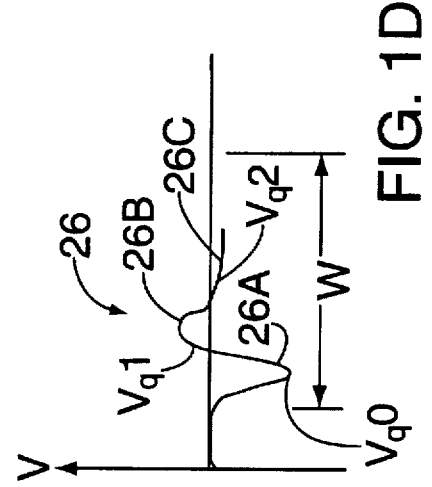
FIG. 1B shows a corresponding signal sensed by an electrode implanted in the tissue of FIG. 1A.
Figure 1D:
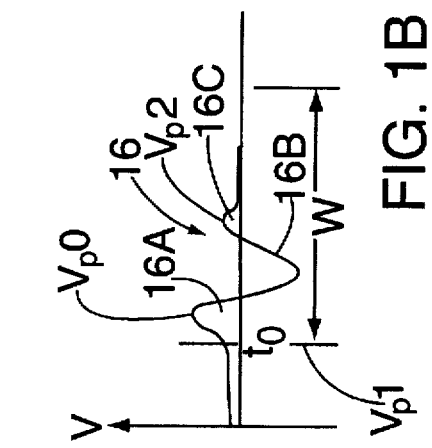
FIG. 1D shows a corresponding signal sensed by an electrode implanted in the tissue of FIG. 1C.

It is important to note that from FIGS. 1B and 1D, that, regardless of the type of depolarization waveform, the corresponding electrical signals have at most three peaks of differing amplitude, two of one polarity, and one of the opposite polarity. A depolarization signal having four peaks of similar amplitude, within a duration of about 70 msec would imply two consecutive depolarization without a refractory or repolarization period separating them. This occurrence is clearly impossible because of the physiological structure of the heart and the mechanism producing the depolarization.

Figure 2A:
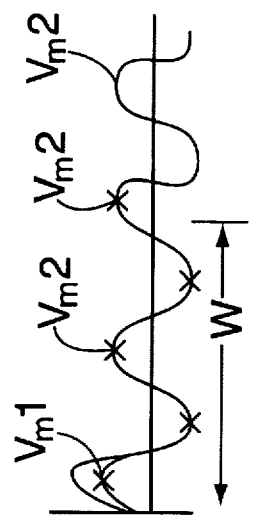
FIG. 2A shows a typical sudden onset 20 Hz EMI signal.
Figure 2B:
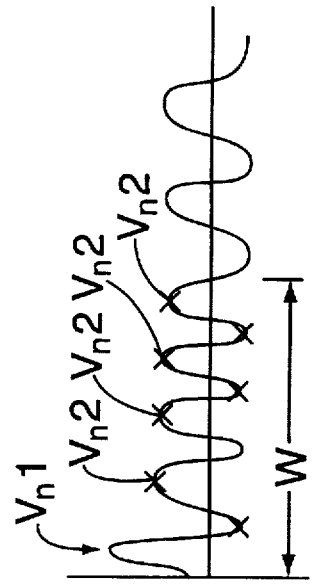
FIG. 2B shows how the 20 Hz signal of FIG. 2A may be sensed by a cardiac implant device through a sensing electrode.

Referring now to FIG. 2A, it can be seen that a typical 20 Hz EMI waveform is a fairly repetitive sinusoidal waveform of amplitude VmO. This EMI signal may be injected into a cardiac sensing by capacitive or inductive coupling or other mechanism. In the cardiac device, this waveform is somewhat distorted mainly due to sudden onset by an internal filter (discussed more fully below) having a center frequency of about 40 Hz. The resulting signal shown in FIG. 2B is still somewhat repetitive.

Figure 2C:
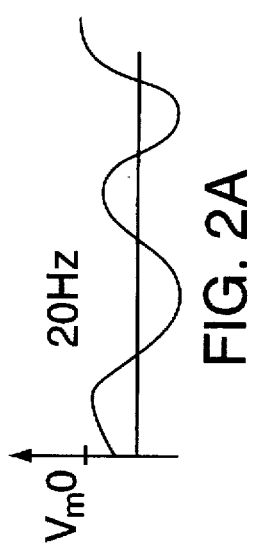
FIG. 2C shows a typical sudden onset 60 Hz EMI signal.

Similarly, a 50 Hz (or 60 Hz) EMI signal may have a nominal amplitude of VnO, as shown in FIG. 2C. After filtering, a waveshape results, shown in FIG. 2D, which is distorted but still fairly repetitive.

The present invention takes advantage of the difference in the structures of the EMI waveforms as compared to the depolarization signals for discriminating the same. One preferred embodiment of the invention consists of means for initiating a noise test window as soon as a signal is detected by the cardiac implant device. During this window, the number and size of peaks is determined. The window must be a sufficient duration to be able to detect at least four or more EMI peaks. Of course, the window should not exceed the natural cardiac delay between depolarizations. The number of peaks is measured, counted and used to determine whether the sensed signal corresponds to a sinus waveform or noise.

Figure 3:
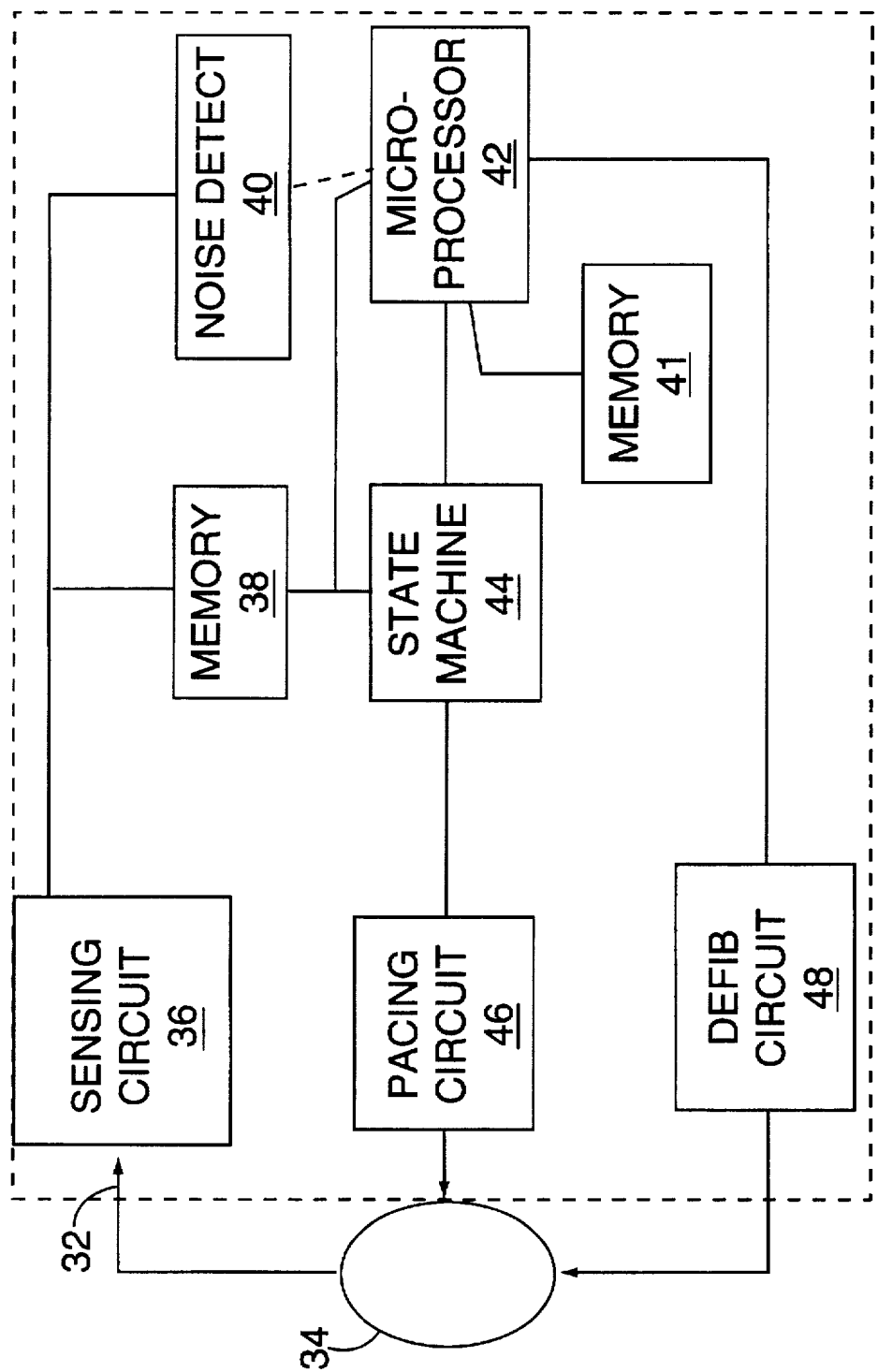
FIG. 3 shows a block diagram form an implantable cardiac device constructed in accordance with this invention.

Referring now to FIG. 3, a cardiac implant device 30 constructed in accordance with this invention consists of a sensing electrode 32 extending into a heart 34 of a patient. The electrode 32 is coupled to a sensing circuit 36 for sensing cardiac activity within the heart. After detection and amplification by the sensing circuit 36, the detected signal v(t) is fed simultaneously to a memory 38 and a noise detection circuit 40. The signal is stored in the memory 38 while the noise detection circuit 40 completes its task. The noise detection circuit 40 makes a determination as to whether the signal v(t) is a relatively clean true cardiac pulse or whether it is contaminated by noise. If the signal is acceptable, it is sent to a microprocessor 42. The microprocessor is associated with another memory 41 for storing programming for the microprocessor 42, as well as data.

It should be understood that the cardiac device 10 of FIG. 3 is shown as a single chamber device for the sake of clarity. However, the invention can be used as well for dual chamber cardiac implants, in which case two sensing electrodes 32 may be used to sense cardiac activity in two cardiac chambers, and two electrodes may be used to apply pacing pulses through electrodes 32. In this case, two different noise detection circuits may be used. Finally, the device 30 may be a cardioverter/defibrillator including a defibrillator circuit 48 also controlled by microprocessor 42. The circuit 48 may be used to provide defibrillation pulses to the heart 34 through an electrode 50.

Figure 4:
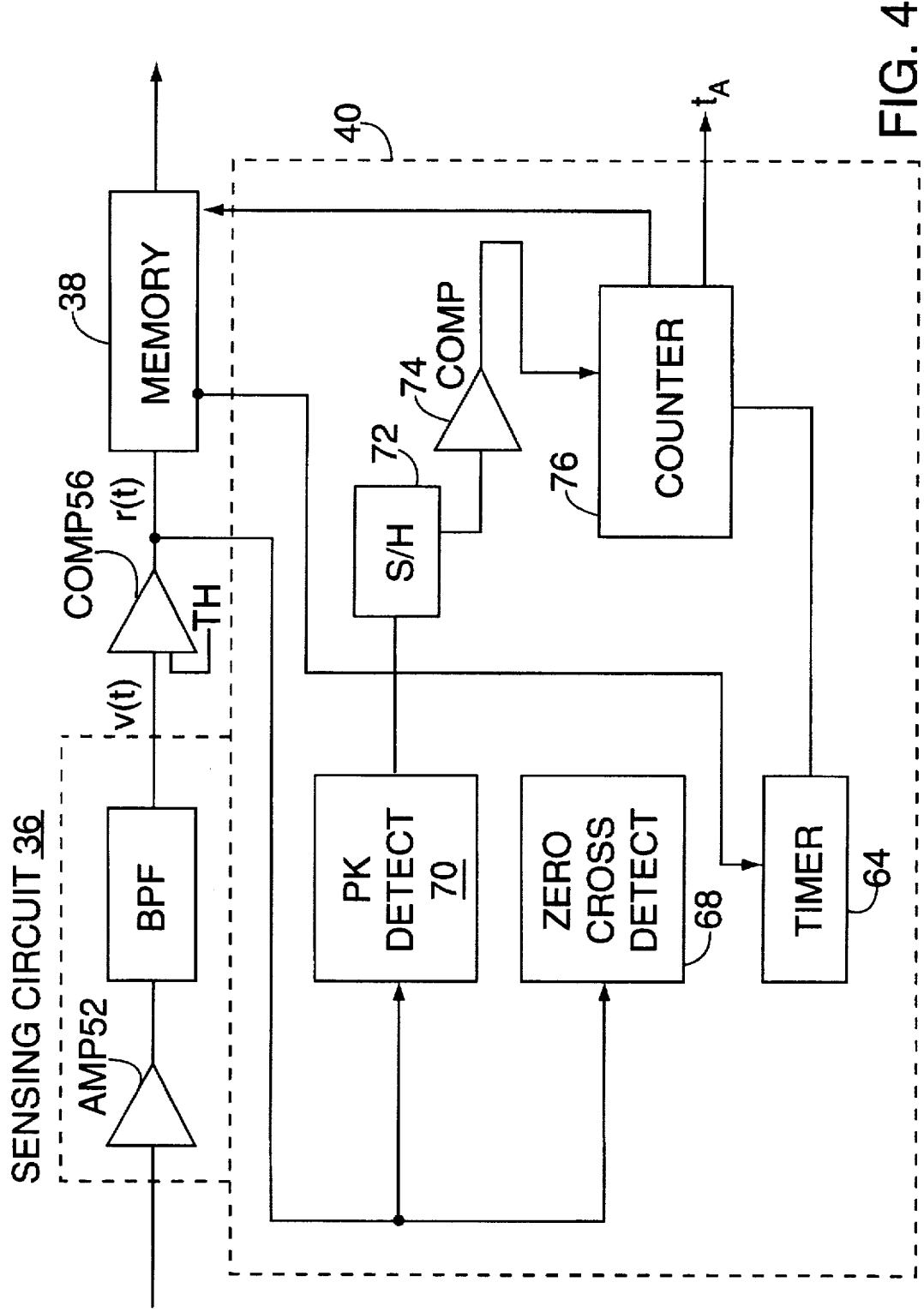
FIG. 4 shows details of the circuitry in the device of FIG. 3 used for noise (EMI) discrimination.

Details of the sensing circuit 36, and noise detection circuit 40 are shown in FIG. 4. The components of these circuits and their operation shall now be described. The sensing circuit includes an amplifier 52 receiving signals from electrode 32, and a band pass filter 54. After amplification by amplifier 52, the filter 54 removes the high frequency components from the signal received from electrode 32. Typically, filter 54 has a center frequency of about 40 Hz. The output of filter 54 is fed as signal v(t) to the comparator 56 and noise detect circuit 40. The signal v(t) can be any one of the signals shown in FIGS. 1B, 1D, 2B or 2D. The output of the sensing circuit 36 is fed to a comparator 56. The comparator 56 compares the amplitude of signal v(t) to a threshold value TH and if the signal's amplitude is above this threshold, then the comparator 56 passes the signal, designated in the drawings as r(t), on to memory 38. The memory 38 receives the signal r(t) from comparator 56 and starts a timer 64, as discussed below to preset conditions for the noise detection circuit 40 to determine whether the signal r(t) should be classified as EMI noise or not.

Importantly, the microprocessor 42 further transmits instructions to the state machine 44 indicating that the signal from memory 38 has been delayed by time ta. The state machine can therefore compensate for the delay induced by the noise detect circuit 40.

The noise detection circuit 40 consists of timer 64, a zero-crossing detector 68, and a peak detector 70, detectors 68 and 70 being coupled to the comparator 56 to receive signal r(t). The circuit 40 further includes a sample-and-hold circuit (S/H) 72, comparator 74, counter 76 and a second comparator 78.

Timer 64 is triggered by memory 38 when an initial deviation from zero (of either polarity) exceeding TH is sensed, the timer generates a pulse on its output having a preselected maximum duration starting at tO. In FIGS. 1B, 1D, 2B and 2D the window W is shown extending from the initial time tO. In essence, the timer sets up an observation window W during which the detection circuit analyzes the signal r(t), depending on the frequency for the EMI expected. For an EMI of 20 Hz W should be at least 100 msec, normally the maximum allowed width. For 60 Hz EMI, W could be 35 msec.

Following this event tO, the peak detector 70 tracks the maximum positive and negative excursion of signal v(t). The zero crossing detector 68 monitors the signal r(t) and resets the peak detector 70 when zero crossings are sensed. The maximum positive and negative peaks of the signal r(t) are fed to the sample-and-hold circuit 72 as well as to the comparator 74. The comparator 74 compares each peak to the peak of the previous wave section provided by S/H circuit 72.

Because of the sudden onset of the EMI, it is possible that the first 20 excursion is much larger than the second. For this reason, the first peak is best ignored. The comparator 74 compares the sequential peaks to differentiate between a sinus beat and noise, as follows. For sinus rhythm the third peak is smaller than the second (for example, the third peak may be less than 70% of the second peak). For example, in FIG. 1B, peak Vp2 is less than 70% of peak Vp1. Similarly, in FIG. 1D, peak Vq2 is less than 70% of peak Vq1.

Figure 2D:
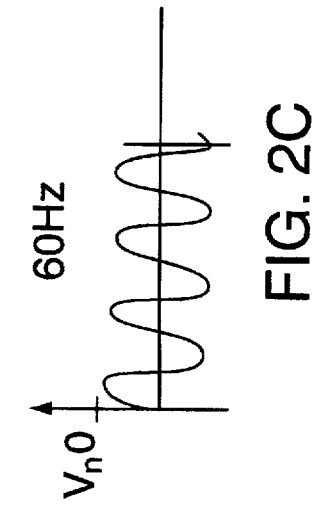
FIG. 2D shows how the 60 Hz signal of FIG. 2C may be sensed by a cardiac implant through a sensing electrode.

However, as seen in FIGS. 2B and 2D, when noise is present either at 20 Hz or 60 Hz, after the first signals Vm1, Vn1, all the subsequent signals Vm2, Vn2, have approximately the same amplitude. Comparator 74 is used to detect signals within a predetermined percentage of the peak amplitudes the preceding signals such as 70%, indicative of repetitive signals. Each time a current peak as indicated by peak detector circuit 70 and the preceding peak indicated by the sample-and-hold circuit 72 are found by comparator 74 to differ by less than 70%, the count in counter 74 is incremented. When the counter 76 reaches a preset count K, for example, four, within window W, the counter 76 resets the timer 64. In this case, the noise detection does not enable the memory 38 to download its intents to the microprocessor because noise (EMI) has been detected and accordingly, the received signal is ignored.

If at the end of the window W, the counter 76 has not reached its preset count K, then it is assumed that the received signal is not EMI. Accordingly, at the end of W, indicated by timer 64, the counter 76 enables the memory 38 to send signal r(t) to the state machine. The state machine then performs a standard operation, taking into account the delay W during which the signal r(t) is held in memory 38.

Figure 5:
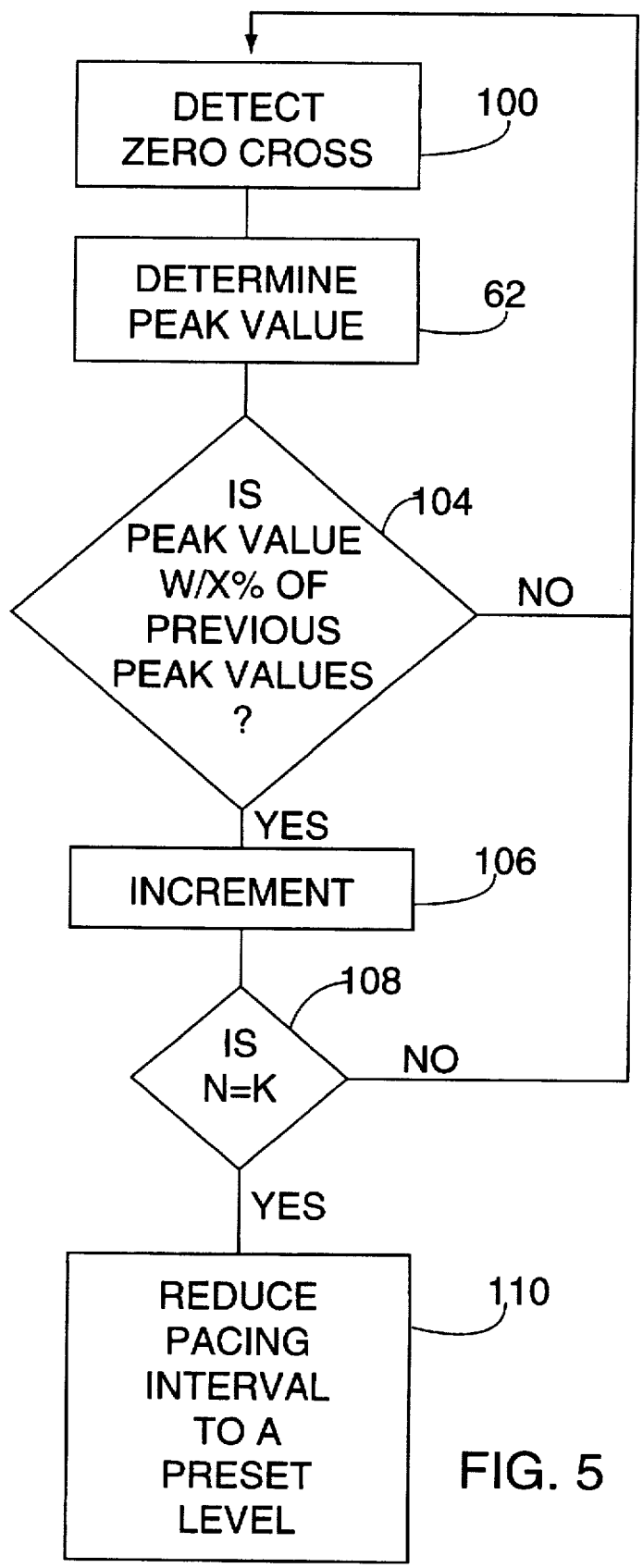
FIG. 5 shows a flowchart showing the operation of the circuitry of FIGS. 3 and 4.

The operation of the pacemaker within a window W is summarized by the flowchart of FIG. 5. In step 100 a zero crossing is detected. In step 102, the peak amplitude is determined between the current and the last zero-crossing. In step 104 the peak value is compared to one or more previous peak values. If it is within a preset range, for example 70%, then this value is candidate for noise. In step 108 a variable N is incremented in counter 76. In step 110 N is tested to see if it has reached preset threshold K. If not, the normal pacing continues.

If in step 108, K is reached, then in step 110 sensing is discontinued and the pacing interval is reduced, i.e., the pacing rate increased to a preselected value, until an external command is received from a programmer to resume normal operation. The programmer can detect that the noise has been detected from the relatively high preset pacing rate. Of course, other indicia of noise may also be used.

In the above discussion, both positive and negative peaks are sensed and counted. Of course, the detection circuit could be modified to count only the positive or only the negative pulses. In this case, the value K would have to be modified accordingly. Moreover, while the above circuitry made use of peak determinations, other features and characteristics of the signals may be extracted and used as well for identifying noise signals, such the number of zero crossing, timing between features, power content, or RMS values and so on.

The sensing and detection circuitry has been described generically to cover both atrial and ventricular activity sensing. Since the signals from these two cardiac chambers, it is expected that the detection circuit has to be tailored specifically for each chamber.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. An implantable pacemaker comprising:
   sensing means for sensing cardiac activity in a cardiac chamber, said sensing means generating corresponding received signals said received signals having repetitive characteristics in the presence of a repetitive noise signal,
   determination means for making a determination if said received signals have said repetitive characteristics; and
   signal processing means for processing said received signals to generate a pacing parameter, said signal processing means being disabled when said repetitive characteristics are detected.

2. The pacemaker of claim 1 wherein signal processing means includes delay means for delaying said received signals from being processed until said determination means makes said determination.

3. The pacemaker of claim 1 wherein said determination means includes feature extraction means for extracting preselected features from said received signal.

4. The pacemaker of claim 2 wherein said determination means makes said determination over a preselected delay period, said pacemaker further comprising compensating means for compensating said received signals for said preselected delay period.

5. An implantable pacemaker comprising:
   an electrode sensing means for sensing an electrical signal on said electrode extending into a cardiac number; wherein said electrical signal has a repetitive characteristic in the presence a repetitive noise;
   signal processing means for processing said electrical signal; and
   control means for selectively disabling said signal processing means, said control means including means for extracting preselected signal features from said electrical signal and determining means for determining in said features said repetitive characteristic of noise, said control means being arranged and constructed for disabling said signal processing means if said repetitive characteristic is determined.

6. The pacemaker of claim 5 wherein said electrical signal has sequential peaks with amplitudes and said control means includes comparing means for comparing said amplitudes wherein two consecutive peaks having substantially amplitudes are indicative of said repetitive noise.

7. The peacemaker of claim 5 herein said electrical signal has peaks and said determining means includes means for counting said peaks.

8. The pacemaker of claim 7 wherein said control means includes memory means for storing said electrical signal for a predetermined period, said processing means being disabled after said predetermined period when said repetitive characteristic is determined.

9. An implantable pacemaker comprising:
   a housing;
   an electrode extending between said housing and a cardiac chamber on implantation and transmitting to said housing an electrical signal indicative of intrinsic activity in said cardiac chamber, said electrical signal having a plurality of consecutive peaks within a predetermined amplitude range when a repetitive noise is present in said cardiac chamber;
   a detector disposed in said housing for detecting said electrical signal, said detector generating an output command when said electrical signal does not include said plurality of consecutive peaks; and
   a processor having a first mode of operation and a second mode of operation, said processor generating first pacing commands in said first mode in response to said output command, said first pacing commands being dependent on said electrical signal; said processor generating in said second mode in the absence of said output command pacing commands which are independent of said electrical signal.

10. The pacemaker of claim 9 further comprising a pacer generating pacing pulses in response to one of said first and second pacing commands.

11. The pacemaker of claim 9 wherein electrical signal has characteristic features and wherein said detector includes a feature extractor for extracting said characteristic features.

12. The pacemaker of claim 9 wherein said detector determines if said electrical signal includes said consecutive peaks from said characteristic features as determined by said feature extractor.

13. The pacemaker of claim 12 wherein said feature extractor includes a counter for counting consecutive peaks of said electrical signal to determine if said repetitive noise is present in said cardiac chamber.

14. The pacemaker of claim 13 wherein said detector includes a timer for defining a window W during which said counter counts said consecutive peaks.

15. The pacemaker of claim 9 wherein said detector generates said output command a predetermined period after said electrical signal is detected and wherein said processor includes a delay device to delay generating pacing parameters corresponding to said current electrical signal during said predetermined period.

* * * * *